(12) United States Patent
Sanchez et al.

(10) Patent No.: US 6,636,758 B2
(45) Date of Patent: Oct. 21, 2003

(54) MARKER WIRE AND PROCESS FOR USING IT

(75) Inventors: Diana Sanchez, Santa Clara, CA (US); Ivan Sepetka, Los Altos, CA (US); Maureen Bensing, Sunnyvale, CA (US); Richard A. Helkowski, Redwood City, CA (US)

(73) Assignee: Concentric Medical, Inc., Mountain View, CA (US)

( * ) Notice: Subject to any disclaimer, the term of this patent is extended or adjusted under 35 U.S.C. 154(b) by 334 days.

(21) Appl. No.: 09/847,769

(22) Filed: May 1, 2001

(65) Prior Publication Data

US 2002/0165450 A1 Nov. 7, 2002

(51) Int. Cl.⁷ .............................. A61B 6/00; A61M 25/09
(52) U.S. Cl. ........................................ 600/434; 600/585
(58) Field of Search .................................. 600/431, 433, 600/434, 585, 435; 604/96.01, 103.06, 103.1, 500, 508, 509, 528, 529; 606/108, 159, 194; 128/898, 899; 607/116, 122; 623/1.11, 1.12, 1.13

(56) References Cited

U.S. PATENT DOCUMENTS

| | | | |
|---|---|---|---|
| 5,163,911 A | 11/1992 | Sirimanne et al. | 604/164.13 |
| 5,253,653 A | 10/1993 | Daigle et al. | 600/585 |
| 5,304,198 A | 4/1994 | Samson | 606/194 |
| 5,334,160 A | 8/1994 | Ellis | 604/167.03 |
| 5,364,354 A | 11/1994 | Walker et al. | 604/103.1 |
| 5,395,334 A | 3/1995 | Keith et al. | 604/103.09 |
| 5,409,004 A | 4/1995 | Sloan | 600/434 |
| 5,484,412 A | 1/1996 | Pierpont | 604/101.03 |
| 5,501,668 A | 3/1996 | Kontos | 604/96.01 |
| 5,512,051 A | 4/1996 | Wang et al. | 604/103.14 |
| 5,527,292 A | 6/1996 | Adams et al. | 604/171 |
| 5,552,818 A | 9/1996 | Agano et al. | 347/133 |
| 5,571,161 A | 11/1996 | Starksen | 607/122 |
| 5,606,981 A | 3/1997 | Tartacower et al. | 600/585 |
| 5,620,649 A | 4/1997 | Trotta | 264/515 |
| 5,628,754 A | 5/1997 | Shevlin et al. | 623/1.11 |
| 5,649,941 A | 7/1997 | Lary | 606/159 |
| 5,653,691 A | 8/1997 | Rupp et al. | 604/103.06 |
| 5,681,336 A | 10/1997 | Clement et al. | 606/159 |
| 5,683,410 A | 11/1997 | Samson | 606/194 |
| 5,702,439 A | 12/1997 | Keith et al. | 604/96.01 |
| 5,713,854 A | 2/1998 | Inderbitzen et al. | 604/509 |
| 5,728,063 A | 3/1998 | Preissman et al. | 604/103.09 |
| 5,752,934 A | 5/1998 | Campbell et al. | 604/96.01 |
| 5,755,690 A | 5/1998 | Saab | 604/103.06 |
| 5,759,173 A | 6/1998 | Preissman et al. | 604/103.07 |
| 5,769,817 A | 6/1998 | Burgmeier | 604/103.06 |
| 5,772,631 A | 6/1998 | Lepor | 604/96.01 |
| 5,776,099 A | 7/1998 | Tremulis | 604/96.01 |
| 5,800,522 A | 9/1998 | Campbell et al. | 128/898 |
| 5,817,053 A | 10/1998 | Agarwal | 604/508 |
| 5,823,995 A | 10/1998 | Fitzmaurice et al. | 604/103.09 |

(List continued on next page.)

FOREIGN PATENT DOCUMENTS

WO    WO 96/30074 A1    10/1996

*Primary Examiner*—Willis R. Wolfe
(74) *Attorney, Agent, or Firm*—Townsend and Townsend and Crew LLP

(57) ABSTRACT

This is a medical device, specifically used in surgery. It is a wire having distal radio-opaque markers and may be used, for instance, in endovascular procedures as a marker wire for estimating or referencing the structural attributes of internal physical features. In addition, the inventive marker wire may be used as a guide wire for a catheter used in endovascular procedures.

20 Claims, 7 Drawing Sheets

U.S. PATENT DOCUMENTS

| | | | | |
|---|---|---|---|---|
| 5,833,631 A | * | 11/1998 | Nguyen | 600/585 |
| 5,833,659 A | | 11/1998 | Kranys | 604/97.01 |
| 5,836,892 A | | 11/1998 | Lorenzo | 600/585 |
| 5,836,912 A | | 11/1998 | Kusleika | 604/96.01 |
| 5,843,051 A | | 12/1998 | Adams et al. | 604/525 |
| 5,860,923 A | | 1/1999 | Lenker et al. | 600/433 |
| 5,868,704 A | | 2/1999 | Campbell et al. | 604/103.11 |
| 5,876,375 A | | 3/1999 | Penny | 604/96.01 |
| 5,879,361 A | | 3/1999 | Nash | 606/159 |
| 5,895,405 A | | 4/1999 | Inderbitzen | 606/194 |
| 5,925,016 A | | 7/1999 | Chornenky et al. | 604/96.01 |
| 5,938,672 A | | 8/1999 | Nash | 606/159 |
| 5,997,558 A | | 12/1999 | Nash | 606/159 |
| 5,997,562 A | | 12/1999 | Zadno-Aziz et al. | 606/194 |
| 6,017,323 A | | 1/2000 | Chee | 604/96.01 |
| 6,027,508 A | | 2/2000 | Ren et al. | 606/108 |
| 6,027,509 A | | 2/2000 | Schatz et al. | 606/108 |
| 6,033,381 A | | 3/2000 | Kontos | 604/164.13 |
| 6,059,751 A | | 5/2000 | Ostapchenko et al. | 604/103.06 |
| 6,068,623 A | | 5/2000 | Zadno-Azizi et al. | 604/530 |
| 6,074,407 A | | 6/2000 | Levine et al. | 606/194 |
| 6,080,170 A | | 6/2000 | Nash et al. | 606/159 |
| 6,090,126 A | | 7/2000 | Burns | 606/194 |
| 6,096,055 A | | 8/2000 | Samson | 606/194 |
| 6,120,477 A | | 9/2000 | Campbell et al. | 604/96.01 |
| 6,122,552 A | | 9/2000 | Tockman et al. | 607/116 |
| 6,139,511 A | * | 10/2000 | Huter et al. | 600/585 |
| 6,146,370 A | | 11/2000 | Barbut | 604/500 |
| 6,146,372 A | | 11/2000 | Leschinsky et al. | 604/510 |
| 6,156,054 A | | 12/2000 | Zadno-Azizi et al. | 606/194 |
| 6,159,195 A | | 12/2000 | Ha et al. | 604/500 |
| 6,159,219 A | | 12/2000 | Ren | 606/108 |
| 6,179,811 B1 | * | 1/2001 | Fugoso et al. | 604/96.01 |
| 6,190,332 B1 | | 2/2001 | Muni et al. | 600/585 |
| 6,193,686 B1 | | 2/2001 | Estrada et al. | 604/103.09 |
| 6,206,852 B1 | | 3/2001 | Lee | 604/96.01 |
| 6,228,072 B1 | * | 5/2001 | Omaleki et al. | 604/529 |
| 6,361,557 B1 | * | 3/2002 | Gittings et al. | 623/1.13 |
| 6,428,512 B1 | | 8/2002 | Anderson et al. | 604/170.01 |

* cited by examiner

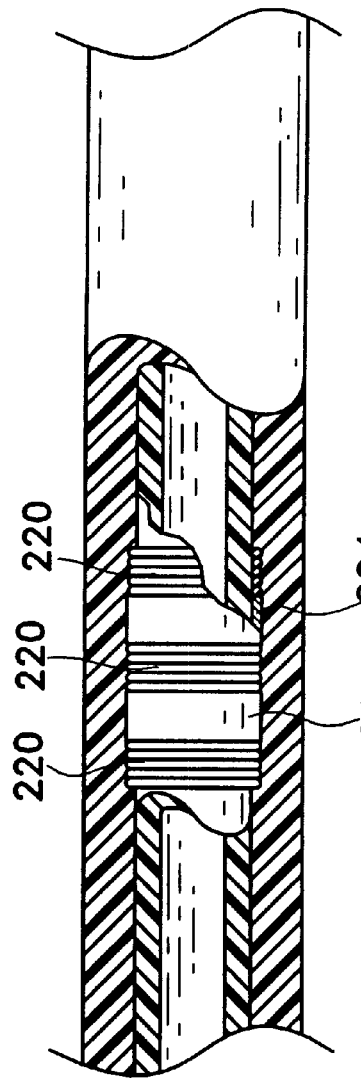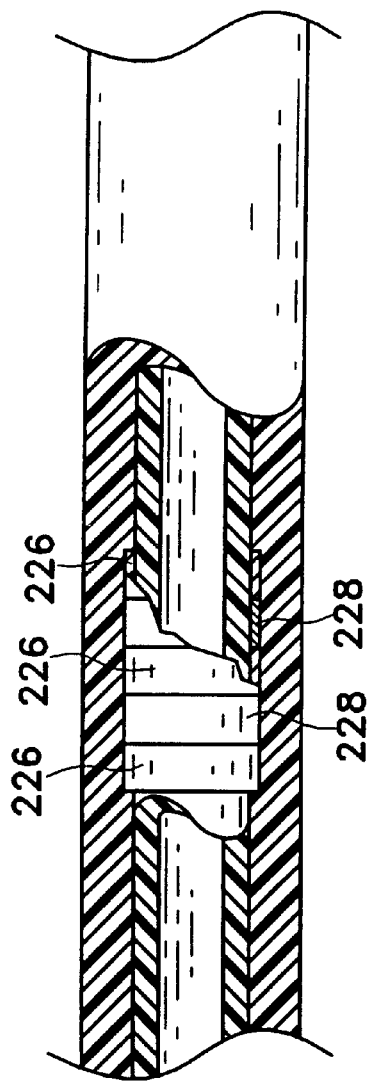

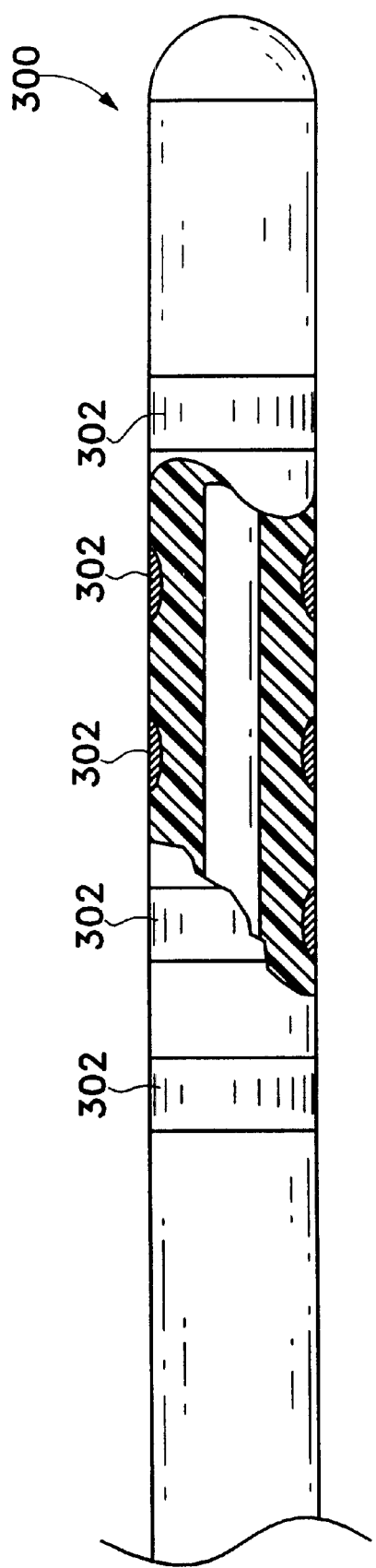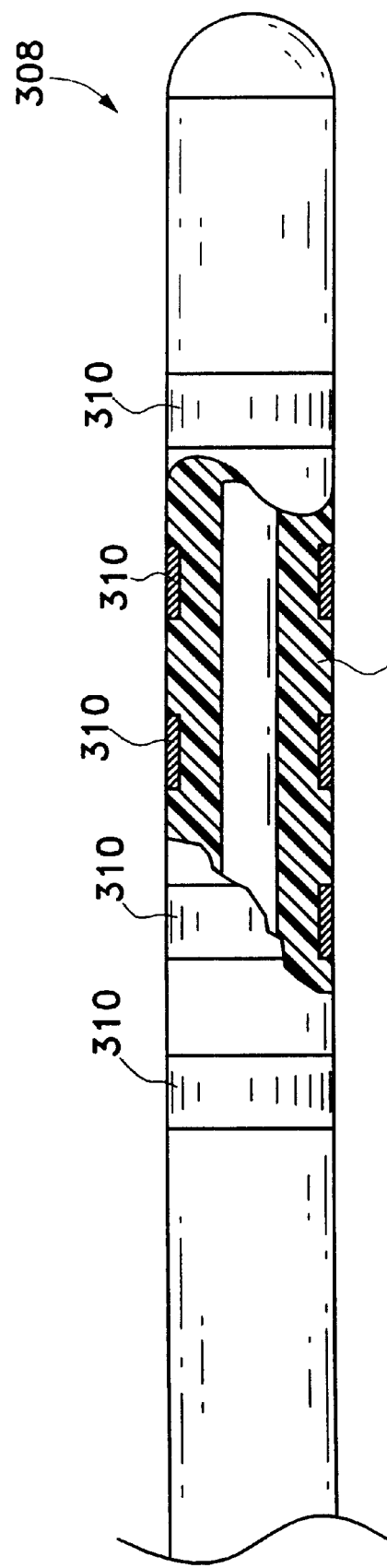
Fig. 3A
Fig. 3B

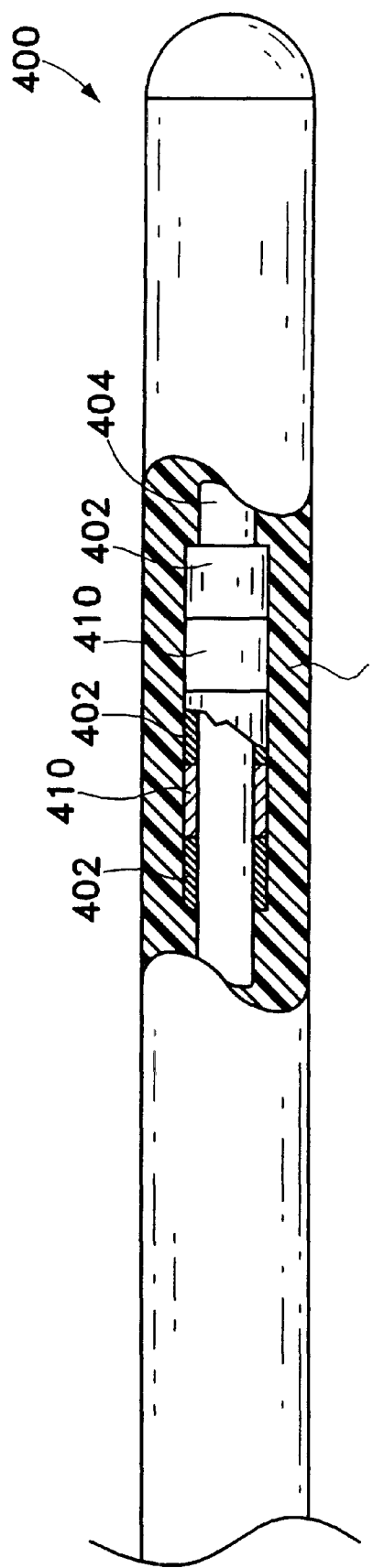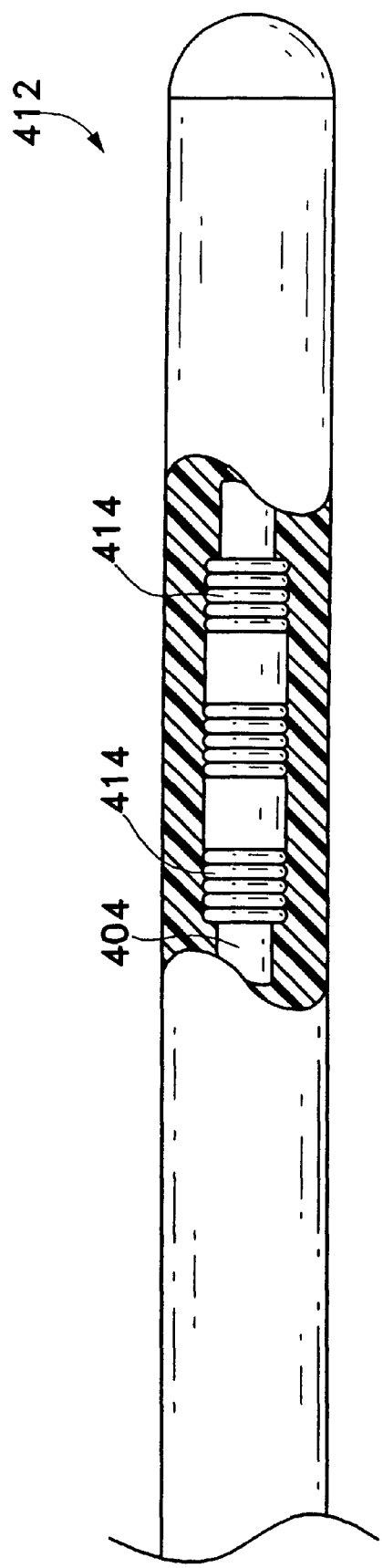

MARKER WIRE AND PROCESS FOR USING IT

FIELD OF THE INVENTION

This invention is a medical device, specifically used in surgery. It is a wire having distal radio-opaque markers and may be used, for instance, in endovascular procedures as a marker wire for estimating or referencing the structural attributes of internal physical features. In addition, the inventive marker wire may be used as a guide wire for a catheter used in endovascular procedures.

BACKGROUND OF THE INVENTION

This invention is a wire having many of the aspects of a guidewire as suitably used with a catheter in accessing remote regions of the human vasculature. More importantly, the inventive wire includes a number of markers situated near the distal tip of the wire that are visible using a fluoroscope or other x-ray apparatus. The markers are spaced in such a way as to allow comparison with some internal physical attribute or feature in the human body.

Placement of radio-opaque markings on surgical guidewires or needles is shown, for instance, in U.S. Pat. No. 5,409,004, to Sloan. Sloan shows the use of a needle useful as a localization device designed to depict the location and depth of lesions found during a mammogram. The markers may be coated onto the needle in such a way that the lesion's specific depth may be reviewed in a fluoroscope or the needle may have specifically formed grooves allowing one to observe that a location is, e.g., 3 cm. from the surface by noting that the needle markers have a set of three rings near the surface of the body.

A catheter having radio-opaque markers for "measurements of the distance between a first target location and a second target location" is shown in U.S. Pat. No. 5,860,923, to Linker et al.

Various guidewires or other medical wires including fluoroscopically viewable sectors are also known.

U.S. Pat. No. 5,253,653, to Daigle et al, shows a guidewire having a series of markers placed near the distal tip of the device typically within the interior of a coil. The markers are mounted on the wire itself by welding, soldering, or brazing.

Similarly, U.S. Pat. No. 5,606,981, to Tartacower et al, describes a device in which the markers variously are placed beneath a polymer sleeve but directly upon the wire core. Alternatively, a radio-opaque coil having a varying pitch along its length. The more tightly wound sections are more visible in the fluoroscope. A polymeric sleeve covers the coil.

U.S. Pat. No. 5,836,892 to Lorenzo, shows a guidewire having two or more radio-opaque marker bands placed directly onto the core wire and separated by plastic tubing segments. The marker bands are also covered by a polymeric sleeving.

Finally, U.S. Pat. No. 6,068,623, to Zadno-Azizi et al, suggests placement of "a series of radio-opaque markers . . . on the body of guidewire (12) as indicated in FIG. 3." It is further suggested that the markers (22) ". . . can be embodied in the wall of catheter (12) or applied as plating to a reduced diameter portion thereof in order to maintain its smooth outer profile."

None of the cited references suggest the marker wire structure as described herein.

SUMMARY OF THE INVENTION

This invention is a marker wire for radiological use. It may be used, for instance, as a reference tool in identifying or estimating structural features in the human body. It is made up of a flexible, elongate core wire having a distal end, a proximal end, an outer surface, and a length extending between the distal end and the proximal end. The core wire has at least one polymeric covering extending proximally from the distal end that is in contact with that outer surface for at least a portion of the core wire length. Desirably, the inventive marker wire has a substantially constant diameter along most of its length.

In particular, the marker wire includes a plurality of radio-opaque markers desirably placed exterior to at least one of the polymeric coverings near the distal end of the core wire. The radio-opaque markers are of a size, shape, and placement suitable for allowing estimation of a distance near or in the body lumen along the marker wire. Estimation of a marker wire distance may be instructive, for instance, in judging or estimating an aneurysm neck size or diameter.

The core wire, preferably stainless steel, may include a metallic ribbon extending distally from the core wire distal end and preferably includes at least one tapered section.

The radio-opaque markers may be helical coils of radio-opaque wire or ribbon or bands of radio-opaque metal, alloy, or polymer containing a radio-opacifier.

The radio-opaque markers may be separated from each other by comparatively radio-lucent spacers such as coils or bands of stainless steel or polymer.

BRIEF DESCRIPTION OF THE DRAWINGS

FIGS. 2B, 2C, and 2D show various placements of and structures for marker bands used in this invention.

FIGS. 3A and 3B show variations of the invention in which the marker bands are placed at the external surface of the inventive marker wire.

FIGS. 4A and 4B shows variations of the invention in which the marker bands are placed on the core wire of the inventive marker wire.

DESCRIPTION OF THE INVENTION

As is noted elsewhere, this invention is a marker wire having a proximal and distal end, but specifically having a plurality of radio-opaque markers located near that distal end. At a minimum, the markers are of one or more sizes and one or more spacings and are arranged in such a way that some selected internal physical feature may be estimated by comparing the physical feature, e.g., an aneurysm neck, to the radio-opaque markers using a fluoroscope.

Figure 1A:
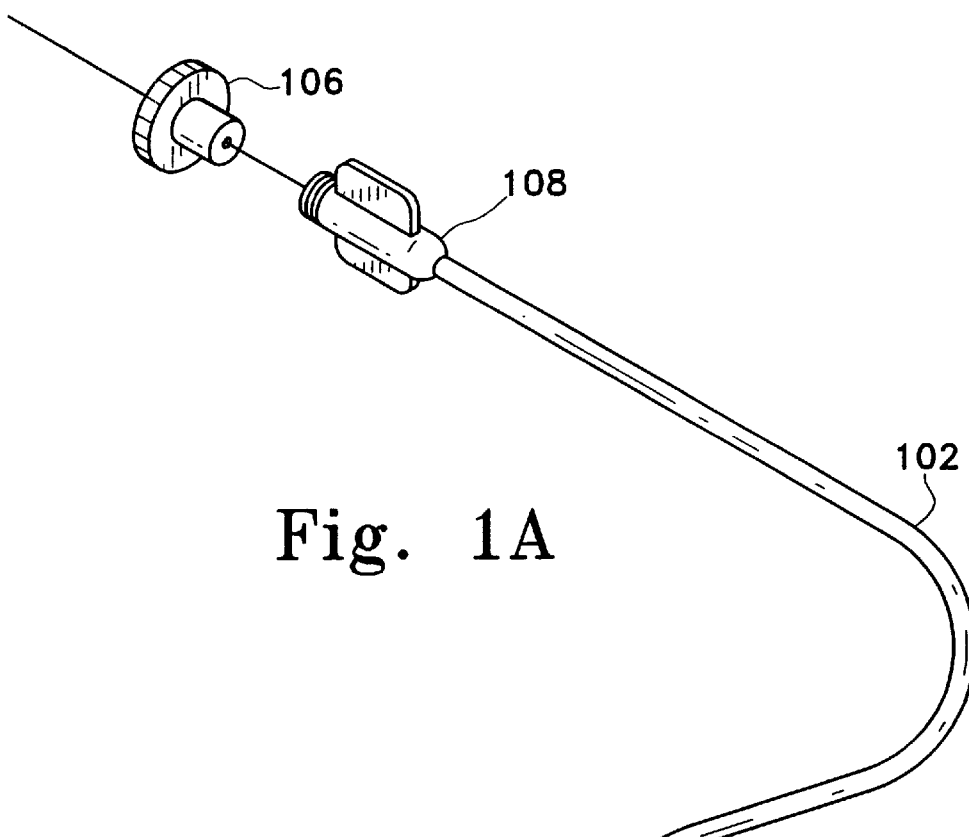
FIG. 1A shows a combination of endovascular catheter used in conjunction with the inventive marker wire.
Figure 1B:
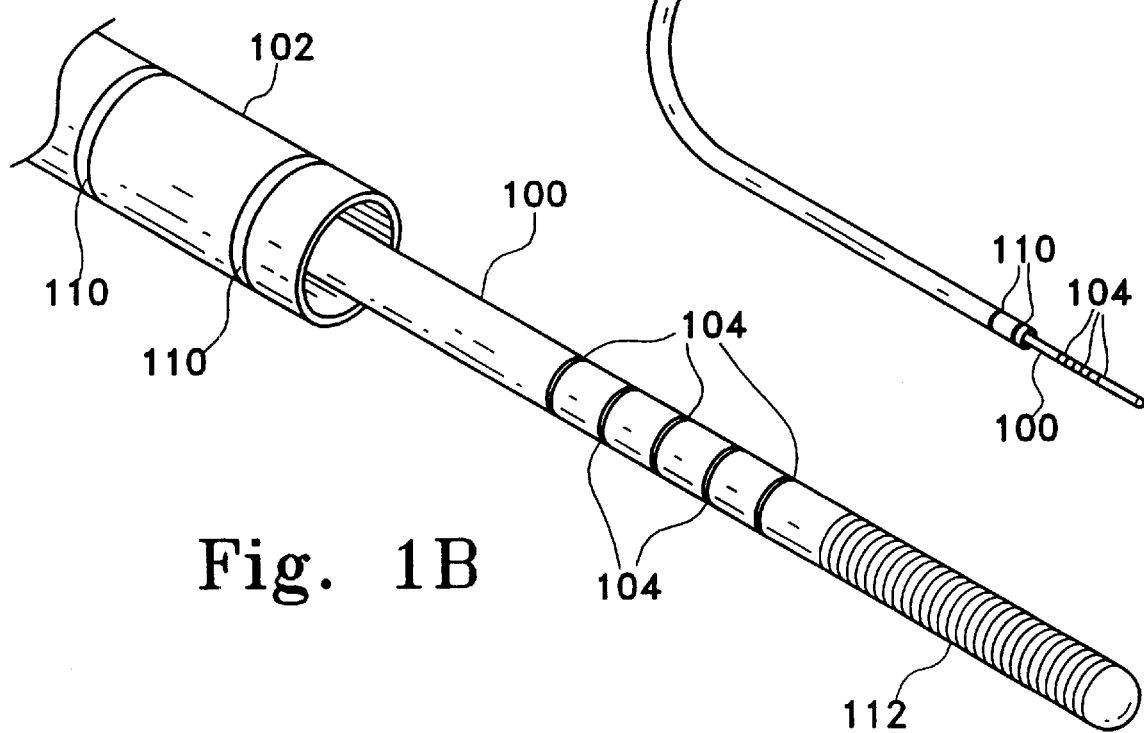
FIG. 1B shows the distal end of catheter shown in FIG. 1A with the inventive marker wire.

The structure of the inventive marker wire may vary as shown below. However, FIGS. 1A and 1B show, in a generic fashion, the overall configuration of the marker wire and its placement in a vascular catheter. The inventive marker wire may be used in a variety of vascular procedures, such as in neurovascular, cardiovascular, and peripheral applications.

As used here, the term "marker bands" is meant to encompass any spaced structure that provides the needed regularity of spacing and is visible in a fluoroscope. The structure may be a band, coil, inked feature, filled polymer structure (variously laid-in, cast, or extruded), etc. so long as they provide the requisite fluoroscopic view in functionally referencing physical structural features.

By "radio-opaque" is meant that, when viewed in a fluoroscope, the radio-opaque bands are visually distinguishable from the adjacent material. As will be seen elsewhere, the term "radio-lucent" is used to describe alloys such as stainless steels, which are visible in most fluoroscopes. We mean only to provide a functional difference in the comparative radio-opacity of the marker bands themselves: the user can see the bands in contrast to the adjacent materials or structure and can identify the bands as the desired marker bands.

FIG. 1A provides a general depiction of the inventive marker wire (100) inserted into a catheter (102). Shown are the distally located radio-opaque marker bands (104). Proximally on the marker wire (100) may be found a torquer (106) for torquing or twisting the marker wire (100) as it is moved through the vasculature.

Also shown in FIG. 1A are typical features of the allied catheter (102), e.g., a proximal fitting (108) such as a Luer-Lok, and one or more radio-opaque catheter marker bands (110). The proximal fitting (108) is normally used for attachment to other fluid control devices, such as those used to introduce radio-opaque dyes into the vasculature. The catheter's distally located marker bands (110) are used variously to locate the distal end of the catheter and to determine the length of or position of vasoocclusive devices, e.g., such as those shown in U.S. Pat. No. 4,994,069, to Richart et al., prior to introducing those vasoocclusive devices into a vascular aneurysm.

FIG. 1B shows a close-up end view of the distal tip of a catheter (102) and marker wire (100) as shown in FIG. 1A. Shown in greater detail are the distally located marker bands (104) on marker wire (100). It is typical, although not required, that the marker bands (104) be located within 4–10 centimeters, preferably within 4–5 centimeters, of the distal tip of the marker wire (100). There may be a formable radio-opaque coil (112) located distally of marker bands (104). The marker bands (104) are multiple and at least two in number. The number of marker bands (104) is at least two and typically is three to eight.

The radial placement of the marker bands may variously be at the surface of the core wire; intermediate in the polymeric layers between the surface of the core wire, e.g., at the surface of a non-exterior polymer layer; or maybe at the exterior of the marker wire assembly. Each of the marker bands' radial placement or positions exhibits a benefit. For instance, the farther that the marker band is placed away from the coil wire, the easier it is to visualize in the fluoroscope. Similarly, the change in axial flexibility of the marker wire in the vicinity of the marker band, is less pronounced when the marker band is placed at a larger radius. The procedure for assembling the marker wire is conversely simpler when the marker band is placed interior to any layer-placed polymer layers. An excellent compromise of visibility and ease of assembly is a structure in which the marker bands are axially situated on an interior polymer layer.

FIGS. 2A–2D show placement of marker bands on an intermediate layer of polymer. The marker bands have various structures.

Figure 2A:
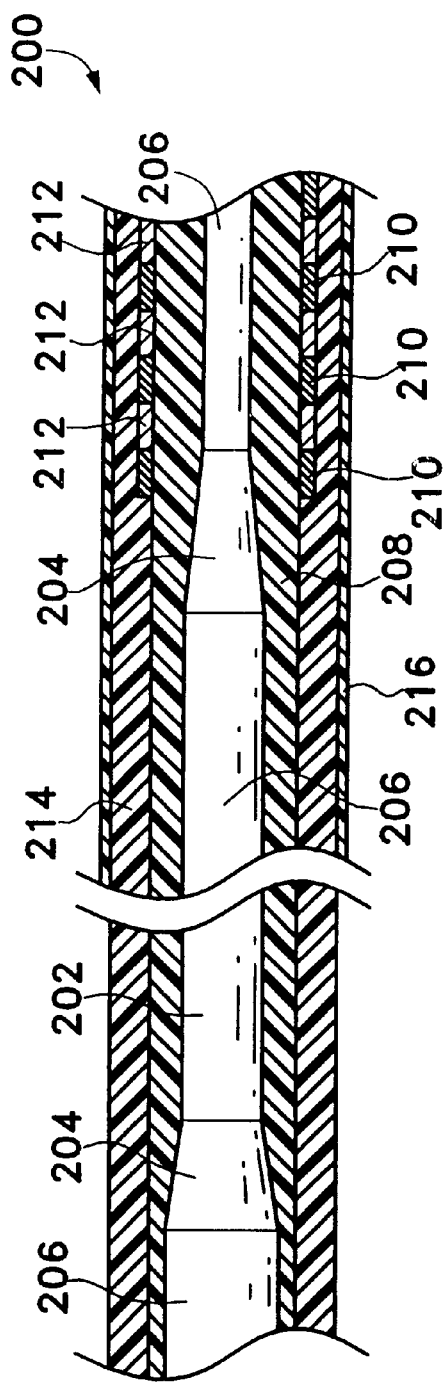
FIG. 2A shows in cross-section a typical construction of a marker wire made according to the invention.

FIG. 2A shows a generic structure of the marker wire assembly (200), having a core wire (202) with a number of tapered regions (204). The core wire (202) is tapered to provide increasing flexibility towards the distal end of the marker wire assembly. Regions of constant diameter (206) are also common. The first layer (208) of a selected polymer is placed on a core wire (202). Desirably, the outer diameter of the first polymer layer (208) is substantially constant in the more distal regions of the wire assembly (200). In any event, FIG. 2A shows placement of radio-opaque marker bands (200) alternating with optional radio-lucent bands (212) on the surface of first polymer layer (208). The marker bands (210) may be placed over a section of constant radius core wire (206) or over a tapered section (204) as desired.

In this variation, another layer of polymer (214) is then applied. Desirably the second polymer layer is applied to provide the substantial constant outer diameter to the marker wire assembly (200) and to smooth any radial protrusions caused by placement of the radio-opaque marker bands (210) and the radio-lucent bands (212). If desired, the outer surface of the second polymer layer (214) may be coated with or treated by a thin layer (216) of a hydrophilic polymer or other lubricity-enhancing material. The first polymer layer (208) and second polymer layer (214) may be those typically used in these services. Typical polymers are polyurethanes (e.g., aliphatic polyurethanes such as Tecoflex, aromatic polyurethanes such as Tecothane, and polyurethane elastomers such as Pellathane), polyesters such as polyethylene terephthalate (PET) and the Nylons, polyvinylchloride (PVC), copolymers such as polyether-amide block co-polymers (Pebax), as well as other known and accepted polymers. The second polymer layer (214) in this variation may be of a material similar to the first layer but may also be comprised of a heat shrinkable material such as a crosslinked polyethylene.

The width and spacing of the radio-opaque bands (210) are desirably 0.75 mm to 10 mm in both width and spacing. Highly preferred, however, for marker bands that are metallic bands is a spacing of 1–10 mm, more preferably 3–10 mm, and a most preferred width of 0.75–1 mm. Highly preferred for marker bands that are metallic, helically wound coils and for radio-opaque polymer bands is a spacing of 1–10 mm more preferably 3–10 mm, and a most preferred width of 1–5 mm. A radio-opaque marker band width of 1 mm is highly desirable for many neurovascular applications. The term "spacing" here typically means a marker-band-center-to-marker-band-center distance.

Figure 2B:
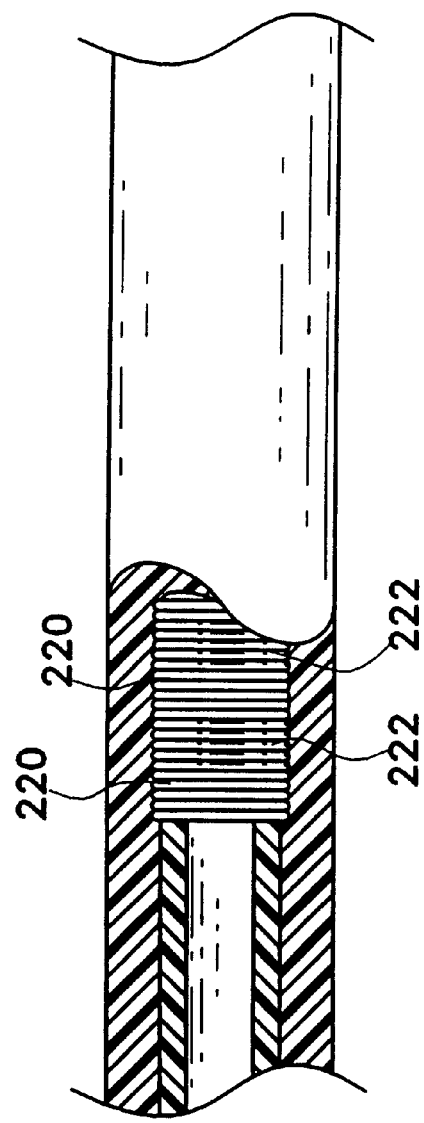

FIG. 2B shows one variation of the inventive device in which helical radio-opaque coils (220) are produced of a material such as gold, platinum, iridium, and other Platinum Group metals and their mixtures and alloys. The helical radio-opaque coils may be made of wires or ribbons. The radio-opaque bands (220) may be alternated with bands (222) of helically wound coils of fibers or wires made of generally (or at least comparatively) radio-lucent materials, e.g., stainless steel or polymers.

FIG. 2C shows a further variation in which radio-opaque coils (220) are separated by, e.g., radio-lucent polymeric bands (224). Such radio-lucent bands (224) may be made of polymers, metals, or alloys such as those discussed above or other suitable radio-lucent materials.

Finally, FIG. 2D shows a variation in which the radio-opaque bands (226) that alternate with the radio-lucent bands (228) are produced of a material such as the radio-opaque metals listed above, e.g., platinum or platinum/iridium alloys, or polymers loaded with radio-opaque materials such as powdered tantalum, powdered tungsten, powdered platinum or similar metals or alloys. Other radio-opaque materials such as bismuth oxide, barium sulfate, or bismuth carbonate, as well as other known radio-opaque materials are also suitable.

The features of each of the variations shown in FIGS. 2A–2D may be mixed as desired. Similarly, the placement of helical coils, polymeric bands (with or without radio-opaque fillers), and metal bands may be used at any radius in the marker wire assembly. Their placement on intermediate polymer layers is preferred, but not required. Similarly, the invention is not limited to constant radius polymeric layers nor to two layers of polymer. There may be multiple layers of polymer on, e.g., any portion of the marker wire FIGS. 3A and 3B show variations of the inventive marker wire in which the radio-opaque marker bands are located at the exterior or outer periphery of the device.

FIG. 3A shows a variation (300) in which the radio-opaque marker bands (302) are comprised of a thermoplastic polymer having a radio-opaque filler, as discussed above. The radius of the device is preferably generally constant in this region of the marker wire. These marker bands (302) may be molded during an extrusion molding procedure or manually placed in an appropriate position and then melted into place. Precision placement of bands (302) using these procedures may be challenging, however.

FIG. 3B shows another variation (308) in which the radio-opaque marker bands (310) are of a material, e.g., a metal or alloy that does not melt during their placement in the surrounding polymer (312). Again, these marker bands (310) may be considered to be at the outer periphery of the device (308) and have an amount of polymer between the interior of the marker bands (310) and the core wire (314).

Of course, the variations of marker band construction and spacer bands shown in conjunction with FIGS. 2A, 2B, 2C, and 2D may be used in conjunction with the variations displayed in FIGS. 3A and 3B.

FIGS. 4A and 4B show variations of the inventive device in which the marker bands are situated on the surface of the core wire.

FIG. 4A shows a first variation (400) of the inventive marker wire in which the alternating radio-opaque marker bands (402) are placed directly upon the core wire (404) and beneath one or more polymeric layers (406). In this variation, the marker bands (402) are bands of radio-opaque material of the type specified above. The radio-opaque marker bands (402) may be axially separated by radio-lucent spaces (410).

FIG. 4B shows a similar variation (412) using helical radio-opaque coils (414) situated on the core wire (404).

Figure 5:
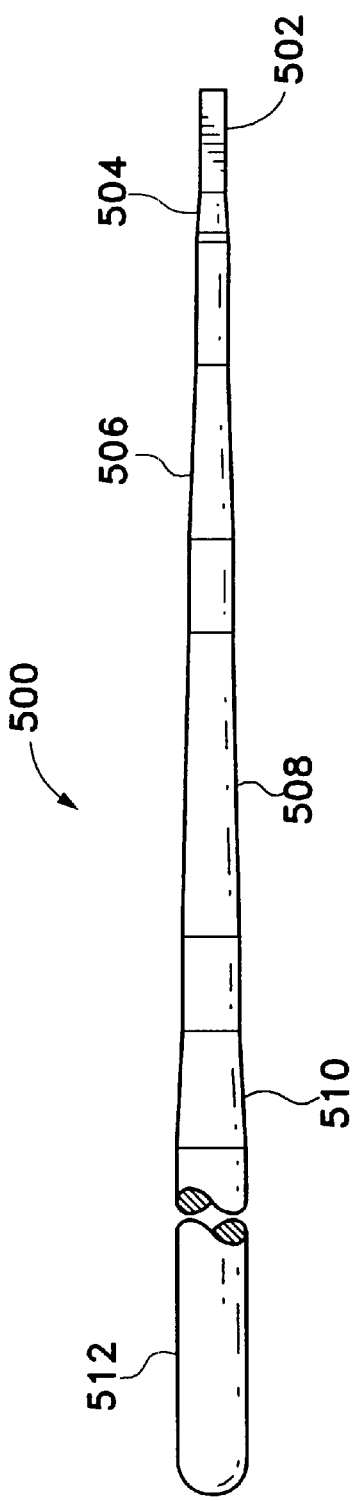
FIGS. 5 and 6 show desirable core wires for use in the inventive marker wire.
Figure 6:
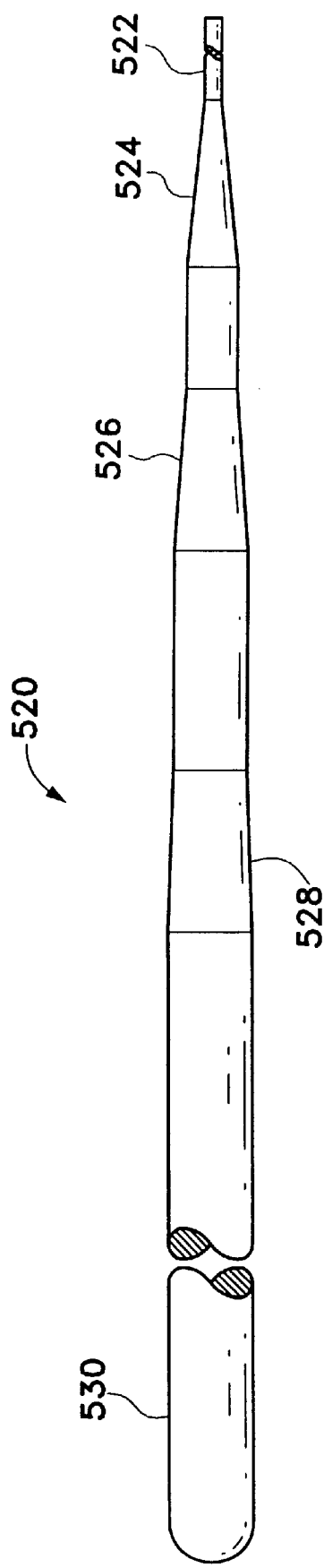

FIGS. 5 and 6 show desired core wires especially suitable for placement in the inventive marker wire described herein. The core wires may be of any convenient material used for guidewires in this service, but preferably are of a suitable stainless steel or superelastic alloy. Most preferred is a stainless steel. Although the invention is in no way limited to any specific size range, finished core wires are typically in the range of 0.008 to 0.040 inches at their widest diameter. Wires for use in the periphery are commonly in the range of 0.018 to 0.038 inches in diameter and neurovascular wires are commonly in the range of 0.010 to 0.018 inches in diameter FIG. 5 shows a core wire particularly useful as a mid-size, neurovascular guide wire or marker wire. Core wire (500) when used, e.g., as a 0.014 inch nominal diameter marker wire, desirably includes a ribbon tip (502) at the most distal end of marker wire assembly (500). This ribbon wire tip (502) permits manual bending of the tip prior to introduction into the catheter and permits steering of the device after it passes the distal end of the catheter. The ribbon tip (502) and its adjacent tapered region (504) is reasonably short for neurovascular use, e.g., 1 to about 2 centimeters. The remainder of the core wire (500) desirably would have 2 or 3 or 4 tapered regions. In this variation, a medium tapered region (506) of 6 to 7 centimeters in length, a second elongated tapered region (508) may be 15 to 30 centimeters in length and the most proximal tapered region (510) might be 3 to 10 centimeters in length. For a 0.014 inch marker wire for neurovascular use, the most proximal portion (512) would have a diameter of typically 0.013 inches. It is typical to coat a substantial portion of this proximal portion (412) with a lubricious coating such as PTFE or polyurethane and at a thickness sufficient to bring the overall diameter to 0.014 inches. The proximal portion in such a service typically would have a length of 75 to 100 centimeters. The overall length of a device such as this would be from 135 to about 225 centimeters, preferably 185 to 210 centimeters. As noted elsewhere herein, core wire (500) may be coated with appropriate polymers and lubricious polymers, as desired, generally to follow the contours of the core wire or, more preferably, to build the outside diameter of the core wire to a uniform diameter, in this instance most preferably 0.014 inches, although the length of each portion of the core wire may be adjusted as desired.

FIG. 6 shows another variation (520) of a core wire suitable for use in this inventive device. Again, FIG. 6 shows a core wire as displayed in the assembly drawings above, e.g., in FIG. 2A and following. This variation may be more suitable for use as a smaller neurovascular marker wire, e.g., 0.010 inches in final diameter. This variation shows a core wire having a ribbon distal tip (522). The device may include a ribbon tip, such as (502) of FIG. 5 or may include only a circular cross-section tip at (522) as is shown in FIG. 6. The variation shown in FIG. 6 has three tapered areas (524), (526), and (528). The variation has a similarly lengthy proximal end (530). The placement of the marker bands and inclusion of the various polymeric layers as discussed above.

Figure 7:
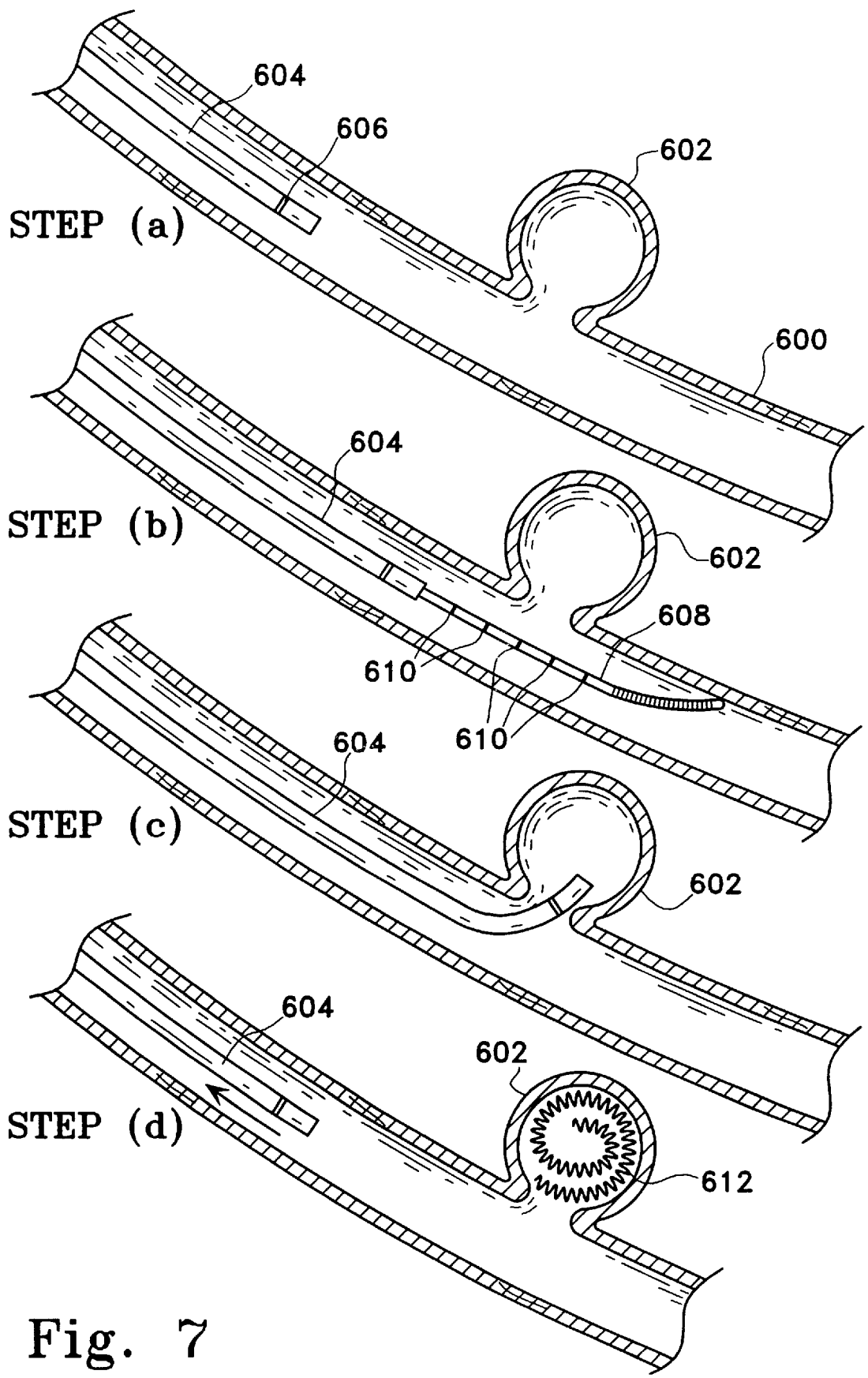
FIG. 7 shows one method of using the inventive marker wire.

The procedure shown in FIG. 7 shows one way in which the inventive marker wire may be used.

Step (a) shows a blood vessel (600), perhaps an artery, having an aneurysm (602) extending from its side. An aneurysm (602) is typically a weakening and ballooning of a region on a blood vessel wall. It is dangerous in that it may leak or rupture, causing a loss of blood into the surrounding tissue. In a brain, a ruptured aneurysm is a vascular accident known as a "stroke."

In any event, step (a) shows the approach of a catheter (604) having a radio-opaque band (606) near its distal tip to an aneurysm. An aneurysm may be detected by an introduction of radio-opaque fluid or dye into the blood vessel.

Step (b) shows a step in which the marker wire (608) is extended from the distal end of a catheter (604). The various marker bands (610) on the distal end of the marker wire (608) are shown. The markers and the respective distances amongst the markers are compared to the diameter of the aneurysm neck. The volume of aneurysm (602) may then be estimated, if such is desired. Once the volume of (602) is known, it may be filled with occluding material to close the aneurysm. One purpose for occluding an aneurysm using the vaso-occlusive coils or other materials known in the prior art, is to isolate the back wall of the aneurysm from the pressure seen in the open blood vessel and thereby lessen the chances that the aneurysm will burst or leak.

Step (c) shows the step of introducing the tip of the catheter (604) into aneurysm (602) and step (d) shows the step of removing catheter (604) after filling aneurysm (602) with a vaso-occlusive device (612) of some kind.

This invention has been described in reference to various illustrative embodiments. However, this description is not intended to be construed in a limiting sense. Various modifications and combinations of the illustrations, as well as other embodiments of the invention, will be apparent to those persons skilled in the art upon reference to the description. It is therefore intended to be appended to claims encompassing any such modifications or embodiments.

We claim as our invention:

1. A wire for radiologically estimating a feature of a structure in a body lumen comprising:
   a.) a flexible, elongate core wire having a distal end, a proximal end, a core radius, and an outer surface, a core wire length extending between the distal end and the proximal end, and having a region near the distal end in which the core radius varies,
   b.) a plurality of radio-opaque markers near the distal end and of a size, shape, and placement to allow estimation of a distance near or in the body lumen, and
   c.) a polymeric covering having a substantially constant radius extending proximally from near the distal end, said polymeric covering being in contact with the outer surface of the core wire for at least a portion of the core wire length that is coextensive with the region near the distal end in which the core radius varies.

2. The wire of claim 1 wherein the polymeric covering is exterior to the plurality of radio-opaque markers.

3. The wire of claim 1 wherein the polymeric covering covers the entire core wire length.

4. The wire of claim 1 further including a metallic ribbon extending distally of the core wire distal end.

5. The wire of claim 1 wherein the region near the distal end in which the core radius varies includes at least one tapered section.

6. The wire of claim 1 wherein the core wire comprises a stainless steel.

7. The wire of claim 1 wherein at least some of the plurality of radio-opaque markers comprise bands of radio-opaque metal, alloy, or polymer containing radio-opacifier.

8. The wire of claim 1 wherein at least some of the plurality of radio-opaque markers comprise helical coils of radio-opaque wire or ribbon.

9. The wire of claim 8 wherein the plurality of radio-opaque markers are separated from each other by substantially radio-lucent spacers.

10. The wire of claim 9 wherein the substantially radio-lucent spacers comprise coils of stainless steel wire.

11. The wire of claim 9 wherein the substantially radio-lucent spacers comprise bands of polymer.

12. A wire for radiologically estimating a distance in a body lumen comprising:
    a.) a flexible, elongate core wire having a distal end, a proximal end, and an outer surface and a length extending between the distal end and the proximal end,
    b.) a polymeric covering extending proximally from the distal end, in contact with the outer surface of the core wire, for at least a portion of the core wire length, and
    c.) a plurality of radio-opaque markers exterior to the polymeric covering near the distal end and of a size, shape and placement to allow estimating of a distance near or in the body lumen.

13. The wire of claim 12 further including a metallic ribbon extending distally of the core wire distal end.

14. The wire of claim 12 wherein the region near the distal end in which the core radius varies includes at least one tapered section.

15. The wire of claim 12 wherein the core wire comprises a stainless steel.

16. The wire of claim 12 wherein at least some of the plurality of radio-opaque markers comprise helical coils of radio-opaque wire or ribbon.

17. The wire of claim 12 wherein at least some of the plurality of radio-opaque markers comprise bands of radio-opaque metal, alloy, or polymer containing radio-opacifier.

18. The wire of claim 16 wherein the plurality of radio-opaque markers are separated from each other by substantially radio-lucent spacers.

19. The wire of claim 18 wherein the substantially radio-lucent spacers comprise coils of stainless steel wire.

20. The wire of claim 18 wherein the substantially radio-lucent spacers comprise bands of polymer.

* * * * *